United States Patent
Chu

(10) Patent No.: US 7,988,976 B1
(45) Date of Patent: Aug. 2, 2011

(54) **METHOD FOR ENHANCING ANTIOXIDANT COMPONENT OF *GRACILARIA TENUISTIPITATA* EXTRACT**

(76) Inventor: Yi-Sheng Chu, Taipei (TW)

( * ) Notice: Subject to any disclaimer, the term of this patent is extended or adjusted under 35 U.S.C. 154(b) by 0 days.

(21) Appl. No.: 12/780,933

(22) Filed: May 17, 2010

(51) Int. Cl.
*A61K 36/02* (2006.01)
(52) U.S. Cl. .................................. 424/195.17
(58) Field of Classification Search .................. None
See application file for complete search history.

(56) References Cited

OTHER PUBLICATIONS

Hao (Shipin Keji (2008), vol. 6, pp. 171-174—translation provided).*

Liu (Shipin Gongye Keji (2005), vol. 26, No. 3, pp. 67-69—translation provided).*

* cited by examiner

*Primary Examiner* — Susan Hoffman

(57) ABSTRACT

A method for enhancing antioxidant components of *Gracilaria tenuistipitata* extract is proposed. The method involves providing an extraction environment of 40° C., and performing cyclic grinding to a *Gracilaria tenuistipitata* solution with an ultrasonic disrupter outputting a vibrating frequency between 20 KHz and 45 KHz for 60 to 120 minutes, so as to stabilize chemical properties of the *Gracilaria tenuistipitata* solution and obtain a *Gracilaria tenuistipitata* extract having more activated protein and phycoerythrin as compared with an extract obtained through the prior art, thereby improving the *Gracilaria tenuistipitata* extract in antioxidative ability.

3 Claims, 1 Drawing Sheet

METHOD FOR ENHANCING ANTIOXIDANT COMPONENT OF *GRACILARIA TENUISTIPITATA* EXTRACT

BACKGROUND OF THE INVENTION

1. Technical Field

The present invention relates to a method for extracting antioxidant from *Gracilaria tenuistipitata*, and more particularly to a method for enhancing antioxidative ability of *Gracilaria tenuistipitata* extract.

2. Description of Related Art

*Gracilaria tenuistipitata* is a large alga of Phylum Rhodophyta, Class Florideophyceae, Order Gigartinales, Family *Gracilaria tenuistipitata*. It can be found in middle to lower parts of intertidal regions and has a color of greenish brown. It has a size between 15 and 20 cm$^3$, in a column shape or a furcata compressed shape or with flanking meristem. There are about 100 species around the world and they mainly live in the Temperate Zone and the Torrid Zone such as in India, Indonesia, China, Taiwan and Japan. *Gracilaria tenuistipitata* is rich in carbohydrate and protein, wherein the carbohydrate is mainly polysaccharide. It is one of the major sources of agar, for extracting algin or being used as a food additive. Researches indicate that *Gracilaria tenuistipitata* can be extracted, through various ways, to obtain active components that promote immune cell proliferation and inhibit mammary, hepateluloar and pancreatic carcinoma cells. Its extract also helps with inhibiting growth of human promyelocytic leukemia cells (HL-60), human erythromyeloblastoid leukemia cells (K562), human-human hybridoma cells (HB4C5), human colon adenocarcinoma grade II cells (HT-29) and Human breast adenocarcinoma cells (MCF-7). Phycoerythrin, in a proper amount, is useful in preventing chromosomal mutation and improving immunocompetence. Traditionally, *Gracilaria tenuistipitata* extract is made by milling and extract a *Gracilaria tenuistipitata* solution in a mill. With the attempt to enhance the extraction rate of polysaccharide, activated protein and phycoerythrin in *Gracilaria tenuistipitata*, hot-water extraction has been performed. However, hot-water extraction still fails to achieve satisfying extraction rate of activated protein and phycoerythrin while adversely affecting to biological activity of these components, thus being disadvantageous in practice.

SUMMARY OF THE INVENTION

The primary objective of the present invention is to provide a method for enhancing antioxidant components of *Gracilaria tenuistipitata* extract, which includes: providing an extraction environment of 40° C., and performing cyclic grinding to a *Gracilaria tenuistipitata* solution with an ultrasonic disrupter outputting a vibrating frequency between 20 KHz and 45 KHz for 60 to 120 minutes, so as to stabilize chemical properties of the *Gracilaria tenuistipitata* solution and obtain a *Gracilaria tenuistipitata* extract having more activated protein and phycoerythrin as compared with an extract obtained through the prior art, thereby improving the *Gracilaria tenuistipitata* extract in antioxidative ability.

DETAILED DESCRIPTION OF THE INVENTION

Figure 1:
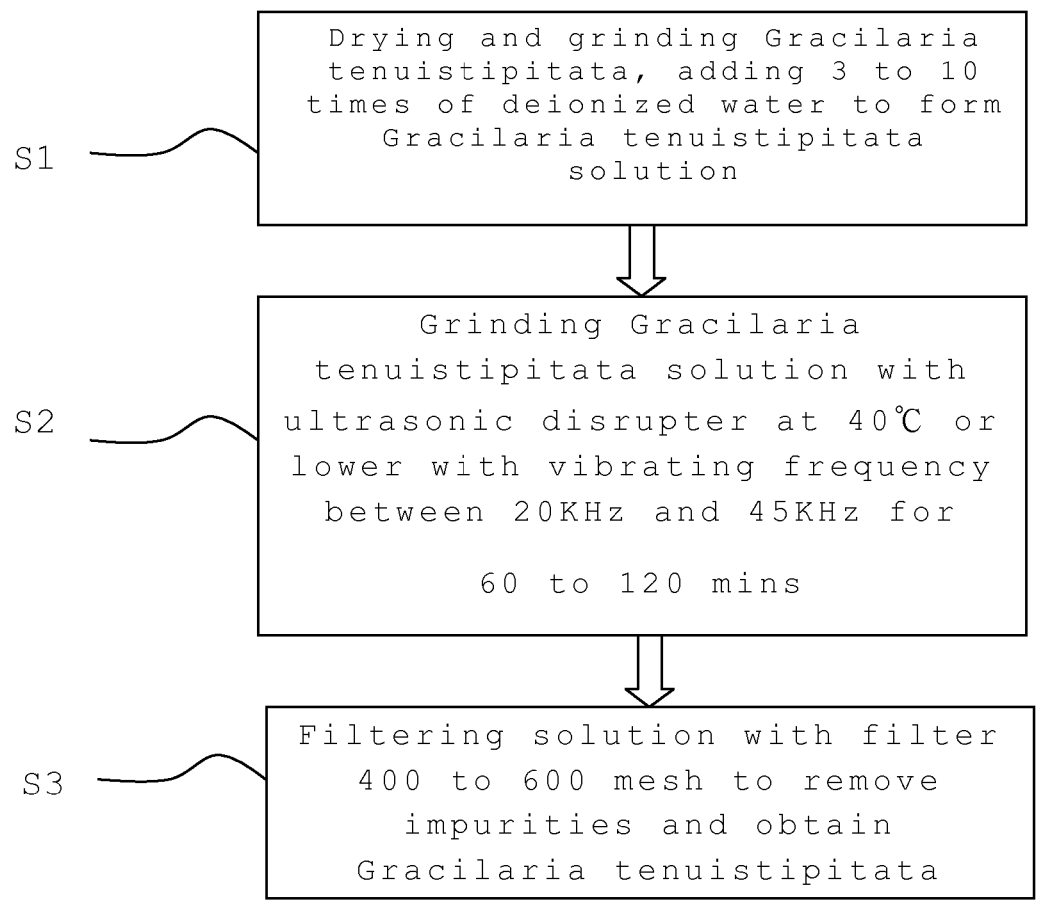
FIG. 1 is a flowchart of a method of the present invention.

For achieving the foregoing objective and effects of the present invention, a preferred embodiment is herein provided to be read with the accompany drawing for people of ordinary skill in the art to understand and in turn implement the present invention.

FIG. 1 is a flowchart of a method of the present invention. As shown clearly in the drawing, a method for enhancing antioxidant components of *Gracilaria tenuistipitata* extract involves the following steps.

(1) Adding a solvent: *Gracilaria tenuistipitata* is first washed to clean and placed in an oven for dehydration. The dried *Gracilaria tenuistipitata* is ground and added with deionized water of an amount equal to three times of the weight of the *Gracilaria tenuistipitata* powder so as to form a *Gracilaria tenuistipitata* solution.

(2) Low-temperature grinding: The solution obtained in the preceding step is put into an average ultrasonic disrupter for cyclic grinding at a temperature not higher than 40° C. with a vibrating frequency between 20 KHz and 45 KHz for 60 to 120 minutes. The maximum output power of the ultrasonic disrupter is 1100 watt, and the high-power ultrasonic energy can break solid particles of *Gracilaria tenuistipitata* into powder with an average particle diameter of a micron scale or the high-power ultrasonic energy can be further adjusted to reduce the average particle diameter to a nano scale. The low temperature during the process helps to stabilize chemical properties of the solution.

(3) Filtering: The solution is filtered with a filter having a mesh size between 400 mm and 600 mm for removing impurities and obtaining the *Gracilaria tenuistipitata* extract containing at least 130 μg/ml of polysaccharide, 1243 μg/ml of *Gracilaria tenuistipitata* protein and 0.41 mg/ml of phycoerythrin.

For clarifying the effect of the method of the present invention, the following experiment was conducted to test contents of polysaccharide, activated protein and phycoerythrin in *Gracilaria tenuistipitata* extract and antioxidative ability of the extract. In the experiment, one control group and two experimental groups were established for comparison, with Control Group basing on the *Gracilaria tenuistipitata* extract of the present invention, Experimental Group A basing on a *Gracilaria tenuistipitata* extract obtained by milling a *Gracilaria tenuistipitata* solution with a mill at 16000 rpm instead of ultrasonic grinding, and Experimental Group B basing on a *Gracilaria tenuistipitata* extract obtained trough the method of the present invention except that the temperature is held between 80° C. and 100° C. The test for activated protein and phycoerythrin included the following three parts:

(I) Analysis of polysaccharide content;
(II) Analysis of activated protein content; and
(III) Analysis of phycoerythrin content.

(1) Analysis of Polysaccharide Content:

(a) 4 ml extracts of Control Group, Experimental Group A and Experimental Group B were respectively added into a 15 ml centrifuge tube preloaded with 8 ml of 99.5% ethanol for 24 hours for precipitation.

(b) The tubes were processed by a centrifuge at 8000 rpm for 3 minutes. The precipitates were dried at 50° C. and re-dissolved in 4 ml pure water. From each of the tubes, 400 μl of the solution was taken and added into an 8 ml glass test tube preloaded with 200 μl of 5% phenol solution.

(c) In each of the glass test tubes, 1 ml of 95% to 97% sulfuric acid solution was added within 10 to 20 seconds and rested at room temperature for 10 minutes before mixed and placed in a bath with 25° C. water for 15 minutes.

(d) The groups were tested for absorbance with a spectrophotometer at 490 nm. The standard curves adapted were those of aqueous sucrose solutions of 0, 0.01, 0.02, 0.03, 0.04 and 0.05 mg/mL. The results are shown in Table 1.

(II) Analysis of Activated Protein Content:

P (a) 5 μl extracts of Control Group, Experimental Group A and Experimental Group B were moved to a 96-well plate and added with 25 μl of a protein-based reagent solution (alkaline copper tartrate).

(b) 200 μl of a diluted Folin-phenol reagent was added to each well and mixed well. The mixture was laid still at room temperature for 15 minutes.

(c) The groups were tested for absorbance with a spectrophotometer at 750 nm. The standard curves were obtained from 0, 0.25, 0.5, 1, 2 and 4 mg/ml of Standard Protein Solution # 1: DC protein assay package. Therein, the standard curve of the absorbance was derived from 40 mg of bovine serum albumin with the standard protein content. The results are shown in Table 1.

(III) Analysis of Phycoerythrin Content:

(a) Samples from Control Group, Experimental Group A and Experimental Group B were processed with a centrifuge and 40 ml of the resultant liquid supernatant of each sample was moved to a 50 ml centrifuge tube and added with 12.7 g ammonium sulphate while stirred slowly and sufficiently.

(b) The samples precipitated at 4° C. in dark for two hours, and processed with the centrifuge at 8000 rpm for 10 minutes. The resultant liquid supernatants were removed to obtain the precipitates as coarse extracts of phycoerythrin.

(c) The coarse extracts were each re-dissolved in 5 ml of deionized water. The volumes were measured to analyze phycoerythrin contents. The results are shown in Table 1.

TABLE 1

Contents of Gracilaria Tenuistipitata Extracts

| | Polysaccharide Content (μg/ml) | Activated Protein Content (μg/ml) | Phycoerythrin Content (mg/ml) |
|---|---|---|---|
| Experimental Group A | 48 | 732 | 0.12 |
| Experimental Group B | 457.8 | 621.1 | 0.09 |
| Control Group | 130 | 1243 | 0.41 |

From the results, we found that the method of the present invention effectively increased the contents of polysaccharide, activated protein and phycoerythrin. While the Gracilaria tenuistipitata extract of Experimental Group B (obtained by using the extraction method of the present invention yet at the temperature between 80° C. and 100° C.) presented a high level of polysaccharide, the contents of activated protein and phycoerythrin did not improve under such a high temperature range. The Gracilaria tenuistipitata extract of Control Group (obtained by using the method of the present invention) had 1243 μg/ml of activated protein, equal to two times of the comparable concentrations of the experimental groups while have 0.41 μg/ml of phycoerythrin, equal to four times of the comparable concentrations of the experimental groups.

Afterward, an experiment for comparison of antioxidative ability of Gracilaria tenuistipitata extracts was conducted. In the experiment, 100 mg of vitamin C was first dissolved in 1 ml pure water, and mixed with a Tris-HCL buffer solution of 100 mM to obtain stand curves of 30, 20, 15, 10, 7.5, 5 and 2.5 μg/ml. Another Tris-HCL buffer solution without the sample was used as a blank group. Before measurement, for ensuring that the measured values of the tested sample could fall in the range of the standard curve, the sample was tested and adjusted to appropriate dilution rates. Then, samples of extracts of Control Group, Experimental Group A and Experimental Group B with different dilution rates and standard vitamin C of the aforementioned concentrations were each measured for 600 μl to be mixed with 600 μl of 2000 mM DPPH. 5 mg of the DPPH was dissolved in 6.345 ml of methanol, and rocked for more than 10 minutes, followed by a 30-minute reaction in dark. Then absorbance was measured with a spectrophotometer at a wavelength of 517 nm. For each sample, three times of measuring were conducted to obtain an average. The equation of its DPPH scavenging rate is:

DPPH scavenging rate=[1−(absorbance of sample/absorbance of Blank Group without sample)]× 100. The calculated results are reflected in Table 2.

TABLE 2

Antioxidative Ability of Gracilaria Tenuistipitata Extracts

| | Experimental Group A | Experimental Group B | Control Group |
|---|---|---|---|
| Antioxidative Ability (μg/ml as Vitamin C) | 7.87 | 7.4 | 12.6 |

From the experiment it was verified that Experimental Group A had an antioxidative ability of 7.8 μg/ml as Vitamin C (i.e. every 1 ml of un-extracted Gracilaria tenuistipitata has an antioxidative ability equal to that of 7.8 μg vitamin C); Experimental Group B had an antioxidative ability of 7.4 μg/ml as Vitamin C (i.e. every 1 ml Gracilaria tenuistipitata extract extracted between 80° C. and 100° C. had an antioxidative ability equal to 7.4 μg vitamin C); and Control Group had an antioxidative ability increased to 12.6 μg/ml as Vitamin C (i.e. every 1 ml of Gracilaria tenuistipitata extract obtained through the method of the present invention had an antioxidative ability equal to 12.6 μg vitamin C). Hence, it is derived that the Gracilaria tenuistipitata extract obtained through the method of the present invention has improved antioxidative ability.

What is claimed is:

1. A method for enhancing antioxidant components of Gracilaria tenuistipitata extract, the method comprising steps of:

(1) drying and grinding Gracilaria tenuistipitata into powder, followed by adding deionized water equal to 3 to 10 times of a weight of the powder to form a Gracilaria tenuistipitata solution;

(2) performing cyclic grinding to the solution in an ultrasonic disrupter with a vibrating frequency between 20 KHz and 45 kHz for 60 to 120 minutes, at an extraction temperature not higher than 40° C. to make an average particle diameter of powder reduced to a micron scale or to a nano scale;

(3) filtering the solution with a filter to obtain the Gracilaria tenuistipitata extract.

2. The method of claim 1, wherein the filter has a mesh size between 400 mm and 600 mm.

3. The method of claim 1, wherein the Gracilaria tenuistipitata extract contains at least 0.41 mg/ml of phycoerythrin.

* * * * *